United States Patent [19]
Lilja et al.

[11] Patent Number: 5,278,047
[45] Date of Patent: Jan. 11, 1994

[54] METHOD OF ANALYSIS, REAGENT COMPOSITION AND USE THEREOF FOR GLUCOSE DETERMINATION

[76] Inventors: Jan E. Lilja, Södra Brunnsvägen 63, S-253 68; Sven-Erik L. Nilsson, Döbeliusvägen 39, S-253 67, both of Helsingborg, Sweden

[21] Appl. No.: 768,249
[22] PCT Filed: Apr. 24, 1990
[86] PCT No.: PCT/SE90/00272
  § 371 Date: Oct. 16, 1991
  § 102(e) Date: Oct. 16, 1991
[87] PCT Pub. No.: WO90/12889
  PCT Pub. Date: Nov. 1, 1990

[30] Foreign Application Priority Data

Apr. 25, 1989 [SE] Sweden .................... 89015150

[51] Int. Cl.$^5$ .................. C12Q 1/00; C12Q 1/54; C12Q 1/62; C12P 19/22
[52] U.S. Cl. .................. 435/14; 435/4; 435/10; 435/11; 435/26; 435/95; 422/57; 422/102
[58] Field of Search .................. 435/14, 4, 10, 11, 26; 436/95; 422/102, 57

[56] References Cited

U.S. PATENT DOCUMENTS

| | | | |
|---|---|---|---|
| 3,964,974 | 6/1976 | Banauch et al. | 435/14 |
| 3,977,944 | 8/1976 | Muller-Matthesius et al. | 435/14 |
| 4,120,755 | 10/1978 | Pierre et al. | 435/14 |
| 4,898,813 | 2/1990 | Albarella et al. | 435/14 |
| 4,975,367 | 12/1990 | Albarella et al. | 435/14 |
| 5,059,394 | 10/1991 | Phillips et al. | 435/14 |

*Primary Examiner*—Michael G. Wityshyn
*Assistant Examiner*—Louise N. Leary
*Attorney, Agent, or Firm*—Kane, Dalsimer, Sullivan, Kurucz, Levy, Eisele and Richard

[57] ABSTRACT

A method, a reagent composition and the use thereof for quantitative determination of total glucose in undiluted whole blood are described. A sample of undiluted whole blood is contacted with a reagent composition which is in dry form and comprises:
glucose dehydrogenase (GDH);
one or more substances from the group consisting of diaphorase, phenazine methosulphate, phenazine ethosulphate, phenazine phenosulphate and Meldola blue;
one or more substances from the group consisting of NAD, NADP, thio-NAD, thio-NADP, nicotinamide-purine dinucleotide, nicotinamide-methylpurine dinucleotide, nicotinamide-2-chloro-methylpurine dinucleotide;
one or more hemolysing substances from the group consisting of phospholipase, hemolysing saponins, and compounds of hydrophilic mono-, di- or tri-saccharides and aliphatic hydrocarbons having 10-16 carbon atoms;
a redox indicator dye; and
optionally mutarotase.

A color change brought about by the reaction of the reagent with glucose in the undiluted whole blood is measured by transmission spectrophotometry.

12 Claims, 4 Drawing Sheets

| REFERENCE METHOD LEVEL mmol/l | METHOD ACC. TO INVENTION LEVEL mmol/l | CV% | TIME TO END-POINT, S |
|---|---|---|---|
| 3.64 | 3.8 | 3.3 | 53 |
| 5.90 | 6.1 | 2.5 | 71 |
| 8.44 | 8.6 | 2.4 | 77 |
| 12.78 | 13.0 | 2.0 | 99 |
| 17.97 | 17.7 | 1.5 | 119 |
| 22.13 | 21.8 | 1.5 | 145 |

CV = COEFFICIENT OF VARIATION

METHOD OF ANALYSIS, REAGENT COMPOSITION AND USE THEREOF FOR GLUCOSE DETERMINATION

The invention relates to glucose determination and more specifically quantitative total glucose determination in undiluted whole blood. The invention is directed to a method of analysis, a reagent composition therefor and the use of this reagent composition.

An important routine analysis in clinical chemistry is blood glucose determination. This type of analysis is used for diagnosis and therapy of diabetes mellitus and for diagnosing a number of other metabolic disorders. Several methods for quantitative glucose determination in whole blood are known.

One of these known methods is based on enzymatic glucose determination with glucose dehydrogenase, and a reagent composition for this method is described in U.S. Pat. No. 4,120,755. This composition comprises a buffer, a pyridine coenzyme and glucose dehydrogenase. The buffer has a pH between 7.9 and 9.0. Another known composition for glucose determination is described in U.S. Pat. No. 3,964,974. This composition primarily consists of a glucose dehydrogenase, specified in respect of purity and type, a pyridine coenzyme such as NAD, a buffer system for maintaining the pH of an aqueous solution of the composition between 6.5 and 8.5, and mutarotase. Neither of these two patents discloses a method or a composition suited for direct quantitative determination of total glucose in undiluted whole blood, that is without a preceding dilution or precipitation step. The only information on how glucose in whole blood can be analysed is given in Example 7 in U.S. Pat. No. 3,964,974, where wet-chemical glucose determination is effected on a sample of whole blood. The proteins are however removed from the whole blood sample before the glucose measurement. By removing the proteins, the red blood cells will also be removed. Thus, the glucose measurement is not effected on whole blood. Reference is here made to p 9, lines 19-24 of the U.S. publication where the reader is explicitly directed away from the idea of retaining the red blood cells in whole blood measurements. After the undiluted blood has been deproteinised in a pre-dilution step, it is mixed with an enzyme/buffer solution. The reaction is then started by adding a coenzyme solution (NAD), whereupon the glucose content is determined. It is stated that the glucose content can be measured, inter alia, by a $NADH_2$-indicating dye or color reaction, e.g. by hydrogenating a tetrazolium salt into a corresponding formazan under the influence of the enzyme diaphorase. The publication does however not suggest using this $NADH_2$-indicating technique for total glucose measurements in a whole blood hemolysate, but only for glucose measurements in blood plasma. Furthermore, in the blood glucose measurements in U.S. Pat. No. 3,964,974, e.g. according to Example 7 thereof, measurements are performed throughout on diluted blood, as opposed to the present invention relying on measurements directly on undiluted blood samples.

It is evident that a simple and quick test for quantitative determination of total glucose in undiluted whole blood would be an important aid in clinical laboratories.

One object of the present invention therefore is to provide a method for quantitative determination of total glucose in undiluted whole blood by transmission spectrophotometry.

Another object is to provide a dry reagent composition for such determination.

The invention relates in particular to total glucose determination in small volumes of undiluted whole blood. In this context, "small volumes" means volumes between 0.1 and 0.001 ml, preferably between 0.02 and 0.001 ml.

According to the invention, the blood preferably is not only undiluted but also untreated.

According to a first aspect of the invention, a method is provided for quantitative determination of total glucose in undiluted whole blood, which method is characterised by contacting a sample, preferably less than 20 microlitre, of undiluted whole blood with a reagent in dry form comprising:

glucose dehydrogenase (GDH);

one or more substances from the group consisting of diaphorase, phenazine methosulphate, phenazine ethosulphate, phenazine phenosulphate and Meldola blue;

one or more substances from the group consisting of NAD, NADP, thio-NAD, thio-NADP, nicotinamide-purine dinucleotide, nicotinamide-methylpurine dinucleotide, nicotinamide-2-chloro-methylpurine dinucleotide;

one or more hemolysing substances from the group consisting of phospholipase, hemolysing saponins, and compounds of hydrophilic mono-, di- or tri-saccharides and aliphatic hydrocarbons having 10-16 carbon atoms;

a redox indicator dye; and optionally mutarotase; and measuring by transmission spectrophotometry a color change brought about by the reaction of the reagent with glucose in the undiluted whole blood.

An aid for carrying out this method is disclosed in U.S. Pat. No. 4,088,448.

According to another aspect of the invention, a reagent composition is provided for quantitative determination of total glucose in undiluted whole blood, which reagent composition is characterised in that it is in dry form and comprises:

glucose dehydrogenase (GDH);

one or more substances from the group consisting of diaphorase, phenazine methosulphate, phenazine ethosulphate, phenazine phenosulphate and Meldola blue;

one or more substances from the group consisting of NAD, NADP, thio-NAD, thio-NADP, nicotinamide-purine dinucleotide, nicotinamide-methylpurine dinucleotide, nicotinamide-2-chloro-6-methylpurine dinucleotide;

one or more hemolysing substances from the group consisting of phospholipase, hemolysing saponins, and compounds of hydrophilic mono-, di- or tri-saccharides and aliphatic hydrocarbons having 10-16 carbon atoms;

a redox indicator dye; and optionally mutarotase.

According to a third aspect of the invention, use is provided of a reagent composition comprising:

glucose dehydrogenase (GDH);

one or more substances from the group consisting of diaphorase, phenazine methosulphate, phenazine ethosulphate, phenazine phenosulphate and Meldola blue;

one or more substances from the group consisting of NAD, NADP, thio-NAD, thio-NADP, nicotinamide-purine dinucleotide, nicotinamide-methylpurine dinucleotide, nicotinamide-2-chloro-methylpurine dinucleotide;

one or more hemolysing substances from the group consisting of phospholipase, hemolysing saponins, and compounds of hydrophilic mono-, di- or tri-saccharides and aliphatic hydrocarbons having 10-16 carbon atoms;

a redox indicator dye; and optionally mutarotase, and which composition is in dry form, for carrying out quantitative determination of total glucose in undiluted whole blood by transmission spectrophotometry.

The contents of the different components in the inventive dry reagent composition are not critical, but calculated on a sample of 1 ml undiluted whole blood may preferably be in the following ranges:

| Substance | Quantity |
| --- | --- |
| Glucose dehydrogenase | 5-500 U (activity units) |
| Diaphorase/Analogs | 1-100 U/0.1-30 mmol |
| NAD and analogs | 1-100 mmol |
| Phospholipase/analogs | 1-1000 U/0.5-70 mg |
| Mutarotase | 0.1-10 U |
| Redox indicator dye | 5-100 mmol |

To the basic composition may be added components optimising the reactive function in different applications. Mutarotase can be used for rapidly converting alpha-glucose to beta-glucose which is the form reacting with glucose dehydrogenase. This is of particular interest when a sample which is not taken directly from the patient should be analysed. Glucose dehydrogenase specifically breaks down beta-glucose. In aqueous solutions, alpha- and beta-glucose are present in a temperature-dependent equilibrium which is established relatively slowly. Since body temperature is relatively constant, mutarotase, which accelerates the establishment of equilibrium, can be excluded from the reagent if samples are taken from body-temperature blood. Besides the cost reduction, the advantages reside in a shortened reaction time and an extended analytical range. A disadvantage is that the calibration solutions and the control solutions should be brought to proper temperature during at least one hour.

Substances having a pH-adjusting effect to ensure that the operating pH is within the activity range of the enzymes can be added to the reagent.

Substances affecting the solubility and durability of the reagent composition can be added to the reagent for different demanding applications.

Glucose dehydrogenase can be obtained from different species having different molar weights, pH optima etc. Here, glucose dehydrogenase only encompasses NAD- or NAD-analog-dependent enzymes, whereas not the types which are oxygen-dependent and operate with kinoid coenzymes, also referred to as glycose dehydrogenase.

Diaphorase is also obtainable from different species, but can be replaced by known substances, such as phenazine methosulphate, Meldola blue etc. There are also other known NAD-analogs, such as the best known NADP, which can be reduced by the glucose/glucose dehydrogenase reaction and transfer the reduction to a dye or color system.

Surface-active substances may also be required for facilitating the wetting of surfaces on an auxiliary appliance. Surface-tension reducing substances can be added for facilitating the coating of hydrophobic plastic surfaces.

To adapt the suspension to different types of coating equipment, the viscosity can be varied by adding suitable high-molecular-weight polymers. The choice of high-molecular-weight polymers is not critical but affects the dissolving rate of the dry reagent. Among usable polymers may be mentioned polyethylene glycol, polyvinyl pyrrolidone, dextran and different cellulose derivatives. The choice of polymers can also be made with a view to stabilising the suspension. On the basis of known preparation techniques from e.g. the food or cosmetics industry, there will hardly be any problems in adapting the reagent to different surfaces.

Surface-tension reducing substances may also have a hemolysing effect, for instance decanoyl-N-methyl glucamide. This is a well-known fact and therefore many substances or combinations of substances can be used. There are also hemolysing substances which are not particularly surface-active, e.g. mellitin and phospholipases.

There are also several known types of color-changing substances which are capable of changing color when affected by NADH and diaphorase. Tetrazolium compounds are advantageous in that the formazan dye is formed irreversibly under normal reaction conditions. 3-(4,5-dimethylthiazole-2-1)-2,5-diphenyl-2H-tetrazolium bromide (MMT) yields a good result in the composition, but many other tetrazolium compounds can be used. It should here be noted that the group from which the hemolysing substance or substances are selected contains only such substances as do not give rise to interfering precipitations in combination with tetrazolium compounds.

The invention will now be described in some Examples with reference to the accompanying drawings.

FIG. 1 schematically shows a reaction formula for the reactions concerned.

Measurements have been performed on whole blood samples prepared with glucose to obtain different glucose levels. The reference method was a glucose dehydrogenase test system from Merck, Gluc-DH (R) method, type 13886, 13887. For the reference method, spectrophotometry was carried out in the UV range, 340 nm according to the accompanying packing specification. The reference method is an analytical method of the wet-chemical type.

EXAMPLE 1

Reagent composition 1 ml
100 U glucose dehydrogenase (Merck)
20 U diaphorase (Merck)
22 mmmol NAD (Merck)
30 mmmol MTT (Merck)
25 mg White saponin (BDH)

5 mg decanoyl-N-methylglucamide
1 ml water subjected to ion-exchange

Figure 2:
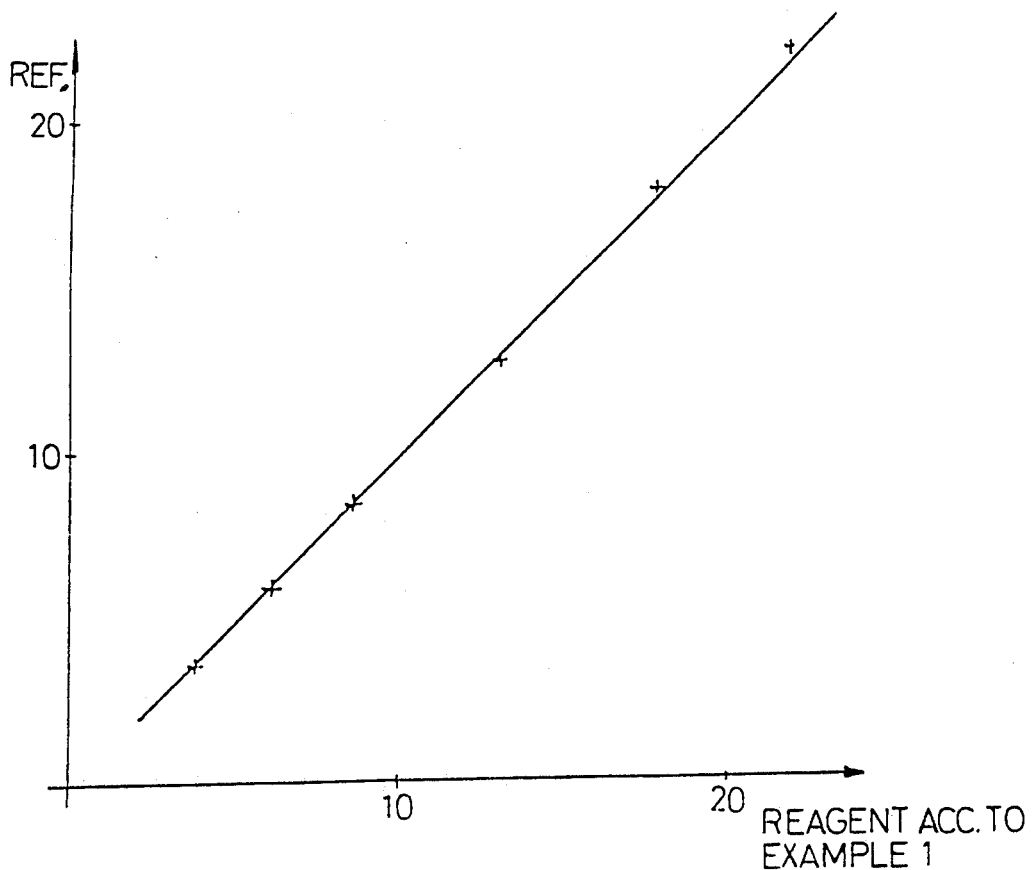
FIG. 2 is a diagram illustrating the spread and correlation to a reference method for "end-point" determination.

This provides a solution which is suitable for freeze-drying in microcuvettes of the injection moulded type described in U.S. Pat. No. 4,088,448, which is commercially available (HemoCue AB). Good reproducibility and linearity were obtained (see FIG. 2). The measurements were conducted at 660 nm with 880 nm as reference wavelength and exhibit "end-point" measurement.

EXAMPLE 2

Reagent composition 1 ml
1 kU glucose dehydrogenase (Merck)
200 U diaphorase (Merck)
220 mmmol NAD (Merck)
0.3 mmol MTT (Merck)
250 mg White saponin (R) (BDH)
50 mg Pluronic P 85 (R) (SERVA)
250 mml water subjected to ion-exchange The components included can be finely divided into a suspension suitable for coating surfaces by different printing techniques, such as silk-screen printing, cylinder printing etc. This type of suspension is suitable for coating microcuvettes of the divided type described in U.S. Pat. No. 4,088,448.

EXAMPLE 3

Figure 1:
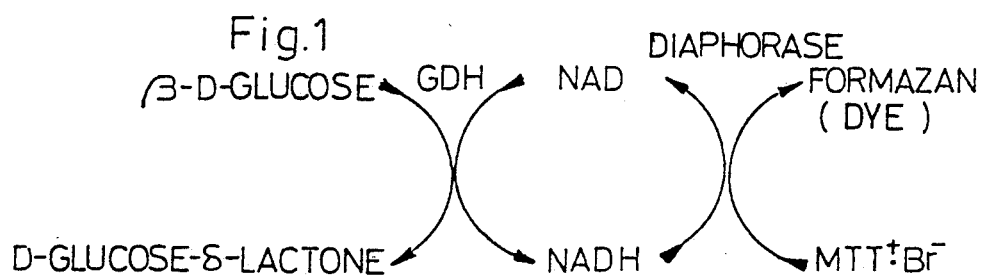
Figure 3:
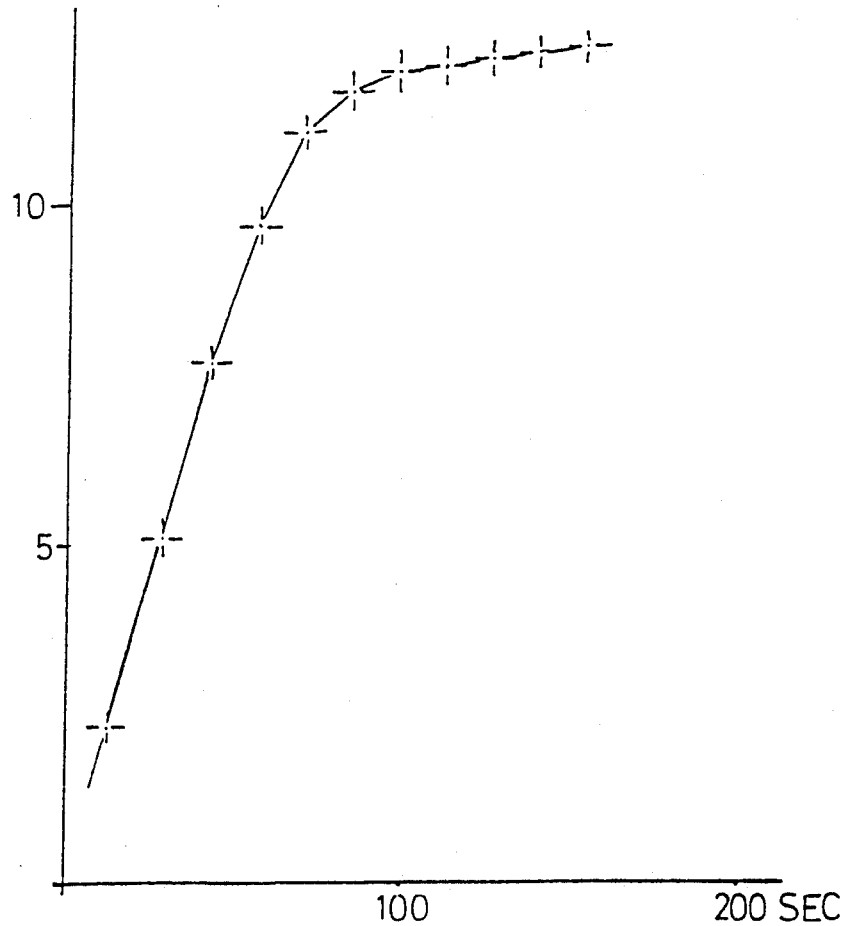
FIG. 3 is a graph of a reaction process in "end-point" determination.
Figure 4:
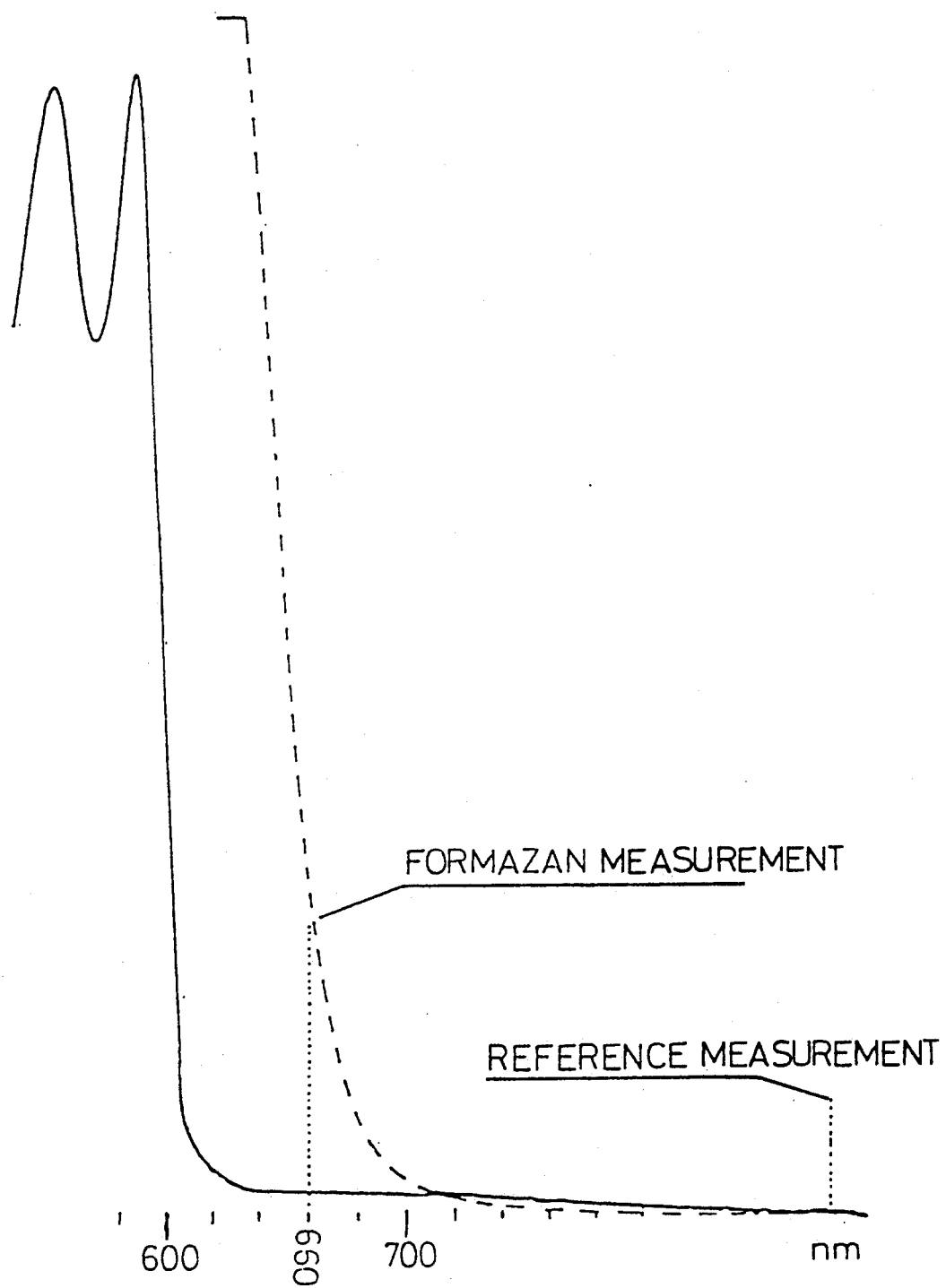
FIG. 4 shows spectra in hemoglobin and MTT-formazan, and indicates measurement and reference wavelengths.

Microcuvettes according to US 4,088,448 made of cellulose acetate/butyrate and having a depth of about 0.15 mm were coated with a reagent composition according to Example 2, by means of a dabber printing machine (4-print). After drying and assembly, the functions of the cuvettes with different whole blood samples were studied. Hemolysis was measured at 660 nm, and the measuring time varied between 20 and 40 s depending on the amount of erythrocytes. The color development was studied at the same wavelength, and for a whole blood sample having a glucose concentration of about 12 mmol/L, an end-point, which was satisfactory from measurement aspects, was attained after 1.5 min (see FIG. 3). FIG. 4 shows the spectrum of hemoglobin and the spectrum of the dye deriving from a whole blood sample with about 12 mmol/L glucose in a cuvette according to Example 3. It clearly appears that there are good possibilities of measuring the formazan dye formed, without any undesired interference by hemoglobin, and also that there is a possibility of measuring turbidity for background compensation outside these spectra. By varying the thickness of the coating, the reaction times will of course be affected and, to some extent, also the maximally determinable concentration.

EXAMPLE 4

Figure 5:
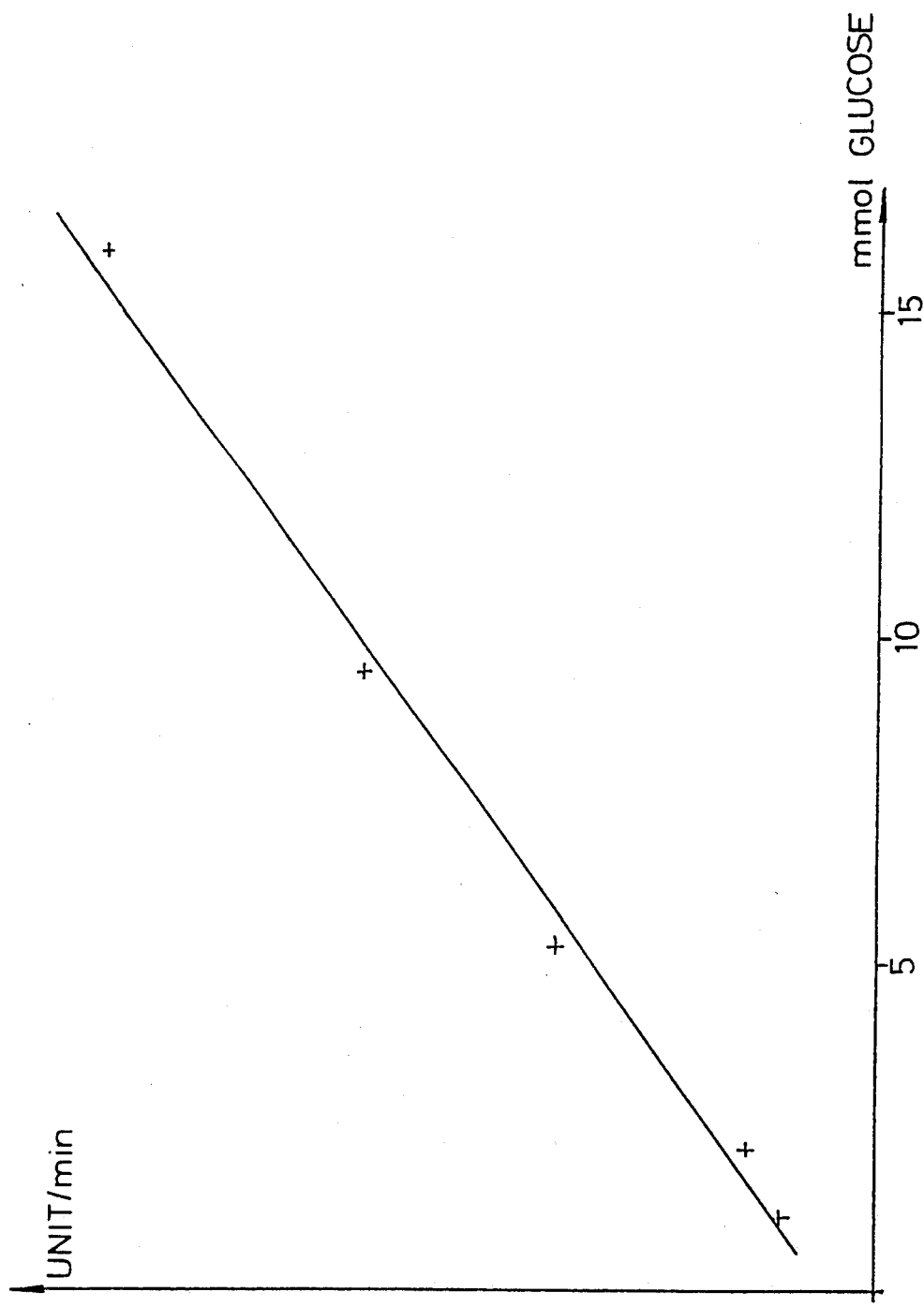
FIG. 5 is a diagram illustrating the correlation to the reference method in kinetic measurements.

Reagent composition 1 ml
25 U glucose dehydrogenase with a maximum amount of polyethylene glycolaldehyde methyl ether 750 linked thereto
5 U diaphorase (Merck)
7 mmol NAD (Merck)
20 mmol MTT (Merck)
25 mg White saponin (R) (Merck)
1 ml water subjected to ion-exchange This provides a solution which is suitable for freeze drying analogously with Example 1. The reagent is adapted for kinetic measurement as opposed to the preceding Examples relating to end-point measurement. The relatively large amount of glucose dehydrogenase depends on the activity reduction which occurs when linking the polymer molecules. Linking polymer molecules to the enzyme increases stability, which is a well-known fact and also desirable for kinetic measurement tests. The optimal polymer type has not been tried out, this Example being merely intended to illustrate the possibility of using polymers. The polyethylene glycol monomethyl ether was converted into aldehyde by reacting with dimethyl sulphoxide and acetic anhydride. After linkage to glucose dehydrogenase in sodium chloride /carbonate buffer pH 10, with an excess of polymer, the mixture was dialysed and concentrated. The enzyme/polymer complex exhibited better stability than the pure enzyme. Examples of results from kinetic measurements with a reagent according to this Example are shown in FIG. 5. The measurements were carried out at 660 nm for 3–3.75 min against reference wavelength 880 nm.

We claim:

1. A method to quantitatively determine the glucose concentration of a sample of undiluted whole blood, comprising contacting a sample of undiluted whole blood with a reagent in dry form in a microcuvette to obtain hemolyzed undiluted whole blood, the reagent comprising:

glucose dehydrogenase (GDH);
   one or more substances from the group consisting of diaphorase, phenazine methosulphate, phenazine ethosulphate, phenazine phenosulphate and Meldola blue;
   one or more substances from the group consisting of NAD, NADP, thio-NAD, thio-NADP, nicotinamide-purine dinucleotide, nicotinamide-methylpurine dinucleo-tide and nicotinamide-2-chloromethylpurine dinucleo-tide;
   one or more hemolyzing substances from the group consisting of phospholipase, hemolyzing saponins, compounds of hydrophilic mono-, di- or tri-saccharides and aliphatic hydrocarbons having 10–16 carbon atoms; and
   a redox indicator dye;

and measuring by transmission spectrophotometry a color change brought about by the reaction of the reagent with glucose in the undiluted whole blood to quantitatively determine the glucose concentration of undiluted whole blood.

2. The method as claimed in claim 1, wherein the sample of undiluted whole blood is a volume of 0.1 to 0.001 ml.

3. A reagent composition to quantitatively determine the total glucose concentration of undiluted whole blood, wherein the reagent composition is in dry form and the reagent composition comprises:

glucose dehydrogenase (GDH);
   one or more substances form the group consisting of diaphorase, phenazine methosulphate, phenazine, ethosulphate, phenazine phenosulphate and Meldola blue;
   one or more substances from the group consisting of NAD, NADP, thio-NAD, thio-NAD, nicotinamide-purine dinucleotide and nicotinamide methylpurine dinucleotide;
   one or more hemolyzing substances from the group consisting of phospholipase, hemolyzing saponins, saccharides and aliphatic hydrocarbons having 10–16 carbon atoms; and
   a redox indicator dye.

4. The reagent composition as claimed in claim 3, wherein the redox indicator dye is a tetrazolium salt.

5. The reagent composition as claimed in claim 3 wherein the reagent composition comprises:
glucose dehydrogenase,
diaphorase,
NAD,
one or more saponins, and
a tetrazolium salt.

6. A reagent composition used to quantitatively determine the glucose concentration of a sample of undiluted whole blood, the reagent composition comprising:
glucose dehydrogenase (GDH);
one or more substances from the group consisting of diaphroase, phenazine methosulphate, phenazine ethosulphate, phenazine phenosulphate and Meldola blue;
one or more substances from the group consisting of NAD, NADP, thio-NAD, thio-NADP, nicotinamide-purine dinucleotide, nicotinamide-methylpurine dinucleotide and nicotinamide-2-chloromethylpurine dinucleotide;
one or more hemolyzing substances from the group consisting of phospholipase, hemolyzing saponins, compounds of hydrophilic mono-, di- or tri-saccharides and aliphatic hydrocarbons having 10-16 carbon atoms; and
a redox indicator dye;
and which composition is in dry form in a microcuvette, for carrying out quantitative determination of total glucose in undiluted whole blood by transmission spectrophotometry to quantitatively determine the glucose concentration of undiluted whole blood.

7. The method as set forth in claim 1 further comprising the step of introducing and freeze drying the reagent in a microcuvette prior to said contacting.

8. The reagent composition of claim 3 wherein said reagent composition is freeze dried in a microcuvette.

9. The method of claim 1 wherein the reagent further comprises mutarotase.

10. The reagent composition as set forth in claim 3 wherein the reagent composition further comprises mutarotase.

11. The reagent composition as set forth in claim 5 wherein the reagent composition further comprises mutarotase.

12. The reagent composition as set forth in claim 6 wherein the reagent composition further comprises mutarotase.

* * * * *